(12) United States Patent
Vazquez Alvarez et al.

(10) Patent No.: US 10,258,707 B2
(45) Date of Patent: Apr. 16, 2019

(54) DIMINISHING GEL COMPOSITIONS AND ASSOCIATED METHODS

(71) Applicant: Henkel IP & Holding GmbH, Duesseldorf (DE)

(72) Inventors: Terannie Vazquez Alvarez, Gilbert, AZ (US); Kevin Hafer, Chandler, AZ (US); Kassandra Nikkhah, Mesa, AZ (US)

(73) Assignee: Henkel IP & Holding GmbH (DE)

( * ) Notice: Subject to any disclaimer, the term of this patent is extended or adjusted under 35 U.S.C. 154(b) by 0 days.

(21) Appl. No.: 15/040,053

(22) Filed: Feb. 10, 2016

(65) Prior Publication Data

US 2017/0224861 A1    Aug. 10, 2017

(51) Int. Cl.
*A61L 9/04* (2006.01)
*A01N 25/04* (2006.01)
*A61L 9/012* (2006.01)
*A01N 25/00* (2006.01)

(52) U.S. Cl.
CPC .............. *A61L 9/012* (2013.01); *A01N 25/00* (2013.01)

(58) Field of Classification Search
None
See application file for complete search history.

(56) References Cited

U.S. PATENT DOCUMENTS

| | | | |
|---|---|---|---|
| 5,871,765 A * | 2/1999 | Johnson | A01M 1/2055 424/406 |
| 7,708,982 B2 | 5/2010 | O'Leary et al. | |
| 8,679,469 B2 | 3/2014 | Allison et al. | |
| 2006/0067963 A1 | 3/2006 | Bell | |
| 2011/0117156 A1 | 5/2011 | Lin et al. | |
| 2012/0219520 A1* | 8/2012 | Allison | A61L 9/012 424/76.4 |

FOREIGN PATENT DOCUMENTS

| | | |
|---|---|---|
| DE | 3239511 A1 | 4/1984 |
| EP | 0904771 A1 | 3/1999 |
| JP | H11128331 A | 5/1999 |
| WO | 3731623 A1 | 9/1997 |

OTHER PUBLICATIONS

"Air Freshener". Database GNPD, MINTAL. Jun. 2014. Database Accession No. 2518477, pp. 1-2. www.gnpd.com XP002769831.
Croda Europe Ltd. "CrystaSense IM Series". 2014, pp. 1-7. www.ulprospector.com/documents/1311758.pdf?bs=1408&b=351546&st=20&r=eu&ind=cleaners. XP002769832.
Croda Europe Ltd. "CrystaSense LP, MP, HP". 2015, pp. 1-7. www.ulprospector.com/documents/1273992.pdf?bs=1408&b=333484&st=20&r=eu&ind=cleaners. XP002769833.
Croda Inc. et al. "The Use of Odour Absorbing Materials Such as Forestall (TM) in a (Polyamide) Gel to Improve Odour Absorption in an Air Freshener or Deodorant". Research Disclosure, vol. 613, No. 7, May 2015, pp. 1-5. ISSN: 0374-4353. XP007144049.
European Search Report EP 17 15 5648 dated May 5, 2017 3 pages.

* cited by examiner

*Primary Examiner* — Ana L. Woodward
(74) *Attorney, Agent, or Firm* — Bojuan Deng (57) ABSTRACT

Diminishing gel compositions are disclosed and described. A diminishing gel composition can include a polymer matrix, a gel-diminishing agent, and a releasable active agent, such as an olfactory agent. The gel-diminishing agent can facilitate a visually noticeable or detectible gradual decrease in volume of the gel composition while in use. The releasable active agent can be released from the gel composition at a rate and amount that is sufficient to produce a desired result, such as an effective olfactory event.

12 Claims, 3 Drawing Sheets

FIG. 1A

* 70% Fragrance Load

DIMINISHING GEL COMPOSITIONS AND ASSOCIATED METHODS

BACKGROUND

Polymer gels have received considerable attention for use in a wide range of practical applications due to the ability to tailor the electrical, mechanical, and optical properties of the materials. For example, polymer gels have been used as scaffolds in tissue engineering, absorbents in disposable diapers, wound dressings, and many other applications. Further, polymer gels can be used as delivery vehicles for therapeutic agents, fragrances, and other active substances. For air freshener applications, these polymer gels offer the benefit of being able to contain relatively high amounts of fragrance per unit volume.

BRIEF DESCRIPTION OF THE DRAWINGS

Invention features and advantages will be apparent from the detailed description which follows, taken in conjunction with the accompanying drawings, which together illustrate, by way of example, various invention embodiments; and, wherein.

DESCRIPTION OF EMBODIMENTS

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this specification and the appended claims, the singular forms "a," "an" and "the" include plural referents unless the context clearly dictates otherwise. Thus, for example, reference to "polymer" can include a plurality of such polymers.

As used herein, a "volatile agent," refers to an agent or substance with a high tendency to vaporize or otherwise change its form or behavior to a certain degree under ambient conditions. For example, most fragrance oils vaporize over time when exposed to the open air. Those of ordinary skill in the art will recognize that different substances can have different degrees of volatility, even under the same or similar conditions.

As used herein, the term "active agent," refers to a volatile agent, ingredient, or substance that provokes a physiological response in an organism coming in contact with the active agent. For example, a fragrance may elicit an olfactory response in an organism, such as a human, when the fragrance reaches the organisms olfactory receptors. Likewise, a pesticide may or pest repellent may cause a physiological response in a pest, such as an insect, which deters the pest or kills it. Fragrances, medicines, pest repellants, pesticides, therapeutic agents and herbicides are all examples of active agents within the scope of the present disclosure.

As used herein, an "olfactory agent," refers to an active agent that acts upon olfactory receptors in an organism, such a human. An exemplary olfactory agent can be a fragrance.

As used herein, a "gel-diminishing agent" refers to an agent, ingredient, or substance included in a gel composition that facilitates a decrease, such as a gradual decrease in volume or size of the gel composition. In some non-limiting examples, the gel-diminishing agent can be a volatile agent that evaporates from the gel composition. In other non-limiting examples, the gel-diminishing agent can increase the porosity of the gel composition to facilitate the evaporation of a volatile agent. In other non-limiting examples, the gel-diminishing agent can increase the release or throw of a volatile agent from the gel composition.

As used herein, the terms "deplete," "depleting," and "depletion," can have their conventional meaning and connote a reduction in an amount. As applied to a releasable active agent held in a gel composition, these terms can refer to the reduction of active agent content in the gel as the active agent is released therefrom. In some aspects, an amount or degree of depleting or depletion can be determined by measuring a current amount of active agent in the gel and comparing it to an original amount of active agent in the gel. In other aspects, the depleting or depletion of active agent from a gel composition can be determined or otherwise gauged by visual observance or inspection of physical changes to the gel composition, such as a reduction in size or volume.

As used herein, the term "exhaust," "exhaustion," and "exhausted," can have their conventional meaning and connote a total depletion, or substantially total depletion of a substance, and can also refer to a reduction of substance to a point where a product or system dependent thereon no longer functions effectively. As applied to a releasable active agent held in a gel composition, these terms can refer to a reduction or depletion of the active agent to the point that the gel composition no longer functions as intended, or functions within specified parameters of usefulness. For example, a fragrant gel composition which no longer throws a useful or beneficial amount of fragrance can be considered to be "exhausted" despite the fact that some amount of fragrance actually remains within the gel.

As used herein, an "effective amount," of an agent, component, or ingredient, can be an amount that is sufficient to achieve or provide a desired or expected outcome or effect. For example, release of an effective amount of an active agent, such as an olfactory agent, from a diminishing gel composition can be an amount that is sufficient to provide a desired physiological effect on an organism, such as an olfactory response. Nearly any parameter, measure, or condition can be placed on achievement of a desired result.

For example, an amount of an olfactory agent that is sufficient to elicit an olfactory response in a human that is about 10 feet or more away from a diminishing gel composition containing the olfactory agent, may be considered to be an effective amount, whereas an amount of olfactory agent that is only sufficient to elicit an olfactory response when the human is within 1 foot or less of the diminishing gel composition may be deemed not to be an effective amount. Alternatively, an effective amount can be measured as a percentage of an active agent released from a diminishing gel composition, and in some cases, as a percentage of active agent released during a specific duration. As one specific example, in some cases an effective amount can include a release of at least 25% of the active agent content (i.e. the amount initially included in the gel composition) over a period of 1 week immediately following activation of the gel composition. In another example, an effective amount can include a release of at least 45%, 50%, or 55% of the active agent content over a period of 5 weeks immediately following activation of the gel composition or over the activated lifetime of the gel composition. In yet another aspect, an effective amount of active agent released can be at least about 10% of the original amount of active agent per week. In some cases, an effective amount can be measured based on the total weight loss of the diminishing gel composition. For example, where the active agent is the primary source of weight loss for the diminishing gel composition, a percent weight loss of at least 20% of the total diminishing gel composition over a period of 1 week immediately following activation of the gel composition can be an effective amount. In another example, an effective amount can include a percent weight loss of at least 35%, 40%, or 45% of the total gel weight over a period of 5 weeks immediately following activation of the gel composition or over the activated lifetime of the gel composition.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this specification it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference in this application may be made to compositions, systems, or methods that provide "improved" or "enhanced" performance. It is to be understood that unless otherwise stated, such "improvement" or "enhancement" is a measure of a benefit obtained based on a comparison to compositions, systems or methods in the prior art. Furthermore, it is to be understood that the degree of improved or enhanced performance may vary between disclosed embodiments and that no equality or consistency in the amount, degree, or realization of improvement or enhancement is to be assumed as universally applicable.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

EXAMPLE EMBODIMENTS

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

Polymer gels have been used to create fragrant products, such as air fresheners, that release a fragrance into a surrounding environment. Most of such fragrant gels suffer from a number of drawbacks and disadvantages. One disadvantage is a lack of an effective end-of-life indicator. Typical polymer gels entrap fragrance or other active agents within the gel matrix. Therefore, while the gel may have exhausted its ability to throw fragrance to a useful degree, it will still provide an olfactory effect when inspected up close. This can mislead a consumer into believing that the gel is still delivering fragrance when, in fact, its useful life has expired. Accordingly, olfactory inspection cannot conclusively determine when a polymer gel product is exhausted and should be replaced. In addition, most polymer gels tend to retain their appearance over time. Therefore, a visual inspection of the gel is not typically sufficient to indicate when a fragrant polymer gel is exhausted and should be replaced.

Another drawback is that polymer gels can exhibit a non-linear release of active agents. In particular, fragrant non-aqueous gel delivery systems have a high initial fragrance release followed by a noticeably rapid decay in the amount of fragrance that is delivered over time. Such uneven release is undesirable.

Despite these drawbacks, polymer gel systems can be tailored for use in almost any application and are capable of holding a large amount of active agent per unit volume. The present inventors have recognized that it would be advantageous to provide polymer gel systems that harness these benefits, while overcoming some or all of the associated drawbacks.

Accordingly, the present disclosure describes gel compositions and systems that provide a number of distinct advantages. In one aspect, gel compositions with one or more characteristics or features that can be used to indicate or signal the end of the gel composition's useful life are provided. In another aspect, gel compositions which provide an even, or substantially even release of an active agent, such as an olfactory agent are provided. Numerous other advantages to the various gel compositions disclosed herein will be apparent from a review of the current specification.

In one example, a gel composition can utilize a visibly detectable change in size, such as a noticeable size reduction, as an indicator that an active agent, such as an olfactory agent, included therein is depleting. In some aspects, the reduction in size can signal exhaustion of the active agent, and therefore the end of the gel composition's useful life. Hence, the diminishing nature of such a gel composition can serve a useful and important purpose.

In one embodiment, a diminishing gel composition can include a polymer matrix, a gel-diminishing agent, and a releasable agent, such as a releasable active agent. Each of these basic elements or ingredients is discussed in turn below.

The polymer matrix of the diminishing gel composition can include a variety of polymers. In one example the polymer can be a polyamine. A variety of suitable polyamines can be used in the diminishing gel composition. Non-limiting examples can include 1,2-diaminocyclohexane, isophorone diamine, meta-xylene diamine, and 1,3-bis(aminomethyl)cyclohexane (1,3-BAC). In some examples, poly(alkyleneoxy)polyamines (polyether amines) can be used. In some examples, the polyether amines can include polyether segments such that greater than 50% by weight of the amine is a polyether derived from oligomerized ethylene oxide, propylene oxide, butylene oxide, tetrahydrofuran, or a combination thereof. In some examples, the polyamine is a material having a polymeric backbone that includes repeating monomer units terminated by amine groups that are not part of the monomer unit.

In some examples, the polyamine can include or can be selected from the group consisting of a polyamide polyamine, an ester terminated polyamine, a tertiary amide terminated polyamine, an ether-based polyamide polyamine, a polyether polyamine, a polyalkyleneoxy polyamine, or a combination thereof. In one example, the polyamine can be a copolymer, such as a block copolymer. In one specific example, the polyamine can be a polyamide polyether block copolymer resulting from reaction of one or more polyalkyleneoxy polyamines with one or more aliphatic polyacids. Such ether-based polyamide polyamines (or "PAPA") can be made by reacting a polyacid or mixture of polyacids with a stoichiometric excess of a polyetherpolyamine admixed with optional lower diamines including piperazine, ethylene diamine, isophorone diamine, hexamethylene diamine, 2-methyl-1,5-pentane diamine, and the like. Suitable poly acids for the preparation of PAPA can include adipic acid, azeleic acid, sebacic acid, dodecanedioic acid, other aliphatic diacids, equivalents thereof, or combinations thereof. Use of such diacids and a majority amount of poly(alkyleneoxy)polyamine (determined as >50% of all amine equivalents present) can provide a polyamide with good solubility in a wide range of carrier solvents.

In some examples, the polyamine can include a blend of two or more polyamines. In one example, at least one of the polyamines in the blend can be a polyamide polyamine. In one example, the blend can include two or more polyamide polyamines.

The polyamines can have a variety of weight average molecular weights (Mw). In one example, the polyamines can have an Mw of from 1,000 to 100,000 daltons. In another example, the polyamine can have an Mw of from 2,000 to 35,000 daltons. In another example, the polyamine can have an Mw of from 4,000 to 30,000 daltons. In some examples, the polydispersity of the polyamide can be from about 1 to 6, or from about 2 to 4.

The amine number of the polyamine can be measured by titration with dilute alcoholic hydrochloric acid and expressed as milliequivalents (meq) KOH/g sample. In one example, the polyamine can have an amine number from about 10 meq KOH/g to about 1200 meq KOH/g. In one example, the polyamine can have an amine number from about 10 meq KOH/g to about 500 meq KOH/g. In one example, the polyamine can have an amine number from about 10 meq KOH/g to about 100 meq KOH/g.

In some examples, the polymer matrix can include a cross-linking agent and the polymer can be cross-linked. A variety of cross-linking agents can be used. In one example, the cross-linking agent can be a chemical compound having two or more functional moieties selected from the group consisting of an epoxy, an isocyanate, an anhydride, an acrylate, and combinations thereof. In one example, the cross-linking agent can be an epoxy. In one example, the cross-linking agent can be a polyanhydride. In one example, the cross-linking agent can be a polyisocyanate. In one aspect, the polyisocyanate can be an aliphatic polyisocyanate. In another aspect, the polyisocanate can include isophorone diisocyanate, bis(4-isocyanato cyclochexyl)methane, and combinations thereof. The cross-linking agent can typically be present in the composition in an amount from about 0.01 wt % to about 20 wt %. In another example, the cross-linking agent can be present in the composition in an amount from about 0.5 wt % to about 10 wt %. In another example, the cross-linking agent can be present in the composition in an amount from about 1 wt % to about 8 wt %.

In one example, the polymer can be present in the composition in an amount from about 1 wt % to about 50 wt %. In another example, the polymer can be present in the composition from about 5 wt % to about 40 wt %. In another example, the polymer can be present in an amount from about 10 wt % to about 30 wt %.

In some examples, the polymer matrix can include a polymer and a carrier solvent. A variety or carrier solvents can be used in connection with the polymer. In one aspect, the carrier solvent can include or be selected from the group consisting of water, an organic solvent, a surfactant, an antioxidant, the like, or a combination thereof. In some examples, the carrier solvent can include or be selected from the group consisting of dipropylene glycol, sodium lauryl sulfate, di(hydrogenated tallow) dimethyl ammonium chloride, cocamido propyl betaine, dibenzyl dimethyl ammonium chloride, a C12-C15 alkyl benzoate, a polysorbate, a sorbitan ester, a lauramine oxide, the like, or a combination thereof.

The carrier solvent can be present in the composition in an amount from about 0.01 wt % to about 30 wt %. In another example, the carrier solvent can be present in the composition in an amount from about 0.05 wt % to about 10 wt %. In another example, the carrier solvent can be present in the composition in an amount from about 1 wt % to about 5 wt %.

The gel-diminishing agent can facilitate or cause the diminishing gel composition to gradually decrease in volume or size while in use. This change in size can be used as a visual indicator of when the gel composition has reached the end of its useful life, for example, when the active agent held therein is exhausted. The gel-diminishing agent can include a variety of suitable ingredients or agents. Some non-limiting examples include a volatile or non-volatile silicone, a linear or branched C9-C16 alkane, neopentyl glycol diheptanoate, an ester of an alkoxylated aromatic alcohol and a fatty carboxylic acid, disteardimonium hectorite, propylene carbonate, triethyl citrate, petroleum distillates, the like, and combinations thereof.

In one specific example, the gel-diminishing agent is a volatile silicone. The volatile silicone can be a cyclical silicone, a linear silicone, or a blend of linear and cyclical silicones. Non-limiting examples of volatile silicones can include or be selected from the group consisting of cyclohexasiloxane, cyclopentasiloxane, cyclotetrasiloxane, cyclic polydimethylsiloxane, linear polydimethylsiloxane, hexamethyldisiloxane, the like, and combinations thereof.

In some examples, the gel-diminishing agent can be present in the diminishing gel composition in an amount of from about 0.01 wt % to about 10 wt %. In some examples, the gel-diminishing agent can be present in the diminishing gel composition in an amount of from about 0.1 wt % to about 8 wt %. In some examples, the gel-diminishing agent can be present in an amount from about 0.5 wt % to about 5 wt %. In some examples, the gel-diminishing agent can be present in an amount sufficient to decrease the volume of the diminishing gel composition by at least 5% to 60%, for example 10%, 20%, 30%, or 40% over a period of about 42 days from activation of the gel-diminishing agent. In some embodiments, specific types and amounts of gel-diminishing agents can be included in the gel composition in order to provide a size reduction in a controlled manner over a predetermined amount of time. For example, a gel composition containing 2 wt % of a gel-diminishing agent can decrease in volume by about 20%, over a period of 30 days, while a gel composition containing 5 wt % of a gel-diminishing agent can decrease in volume by about 50% over a period of 30 days. In other examples, a gel composition containing 3 wt % of a gel-diminishing agent can decrease in volume by about 20% over a period of four weeks.

In some embodiments, the gel-diminishing agent can effectively extend a release period of the releasable agent as compared to the same gel composition without the diminishing gel agent. For example, a diminishing gel composition with a gel-diminishing agent can extend an effective release period of the releasable agent by at least 10%, 20%, 30%, or 40% or more as compared to the same gel composition without the gel-diminishing agent. In further embodiments, a diminishing gel composition with a gel-diminishing agent can release a releasable agent, such as an active agent, held therein at a rate that is substantially higher and more even or consistent than a comparable gel without the gel-diminishing agent.

The releasable agent can be any releasable agent, and specific agents can be selected in order to produce a product of specific use. One example of a suitable releasable agent is a releasable olfactory agent. One example of an olfactory agent is a fragrance. Other active agents such as a pest repellent (e.g. insect repellent) a pesticide, an herbicide, a therapeutic agent, a medicinal agent, or a combination thereof can be used as a suitable releasable agent. Thus, is some examples, the releasable agent can include or be selected from the group consisting of a releasable olfactory agent, a pesticide, a pest repellant, an herbicide, a therapeutic agent, the like, and combinations thereof. Again, specific releasable agents can be selected in order to produce a product with a specific function or purpose.

In one example, the releasable agent or releasable olfactory agent can be a fragrance. Fragrances are well known in the art and the fragrance used in the current composition can include any suitable fragrance or combination of fragrances. For example, fragrances can include any suitable perfume, cologne, fragrance oil, essential oil, the like, or combinations thereof. The fragrance can be formulated to have at least a top note, a middle note, and a bottom note, or any desired combination thereof. In short, nearly any fragrance that interacts suitably with the diminishing gel compositions disclosed herein can be used.

In another example, the releasable agent can be an active agent (i.e. a releasable active agent) such as a pest repellent. Pest repellents are generally known in the art and can include any suitable pest repellent. In some examples, the pest repellent can include an essential oil, such as citronella oil, peppermint oil, basil oil, lemongrass oil, cinnamon oil, pine oil, juniper oil, oregano oil, grapefruit oil, lemon oil, the like, and combinations thereof. Pest repellents can also include N,N-Diethyl-meta-toluamide (DEET), picaridin, 3-[N-Butyl-N-acetyl]-aminopropionic acid ethyl ester (IR3535), dimethyl carbate, ethylhexanediol, dimethyl phthalate, metofluthrin, indalone, tricyclodecenyl allyl ether, the like, and combinations thereof. Nearly any pest repellent that is compatible with the present diminishing gel compositions can be used. In some embodiments, the pest repellent can be selected or formulated to repel insects, rodents, snakes, lizards, or any other desired pest.

In some examples, the releasable agent can be present in the diminishing gel composition in an amount from about 0.01 wt % to about 90 wt %. In one example, the releasable agent can be present in the diminishing gel composition in an amount from about 5 wt % to about 80 wt %. In another example, the releasable agent can be present in the diminishing gel composition in an amount from about 10 wt % to about 70 wt %.

The releasable agent can be released from the composition in an effective amount. In some examples, when the releasable agent is a releasable olfactory agent the release rate and amount can be sufficient to produce an effective olfactory event.

The diminishing gel composition can be included in a system for emitting a releasable agent such as a releasable olfactory agent or active agent. The system can also include a gas-tight container. The diminishing gel composition can be contained within the gas-tight container until the container is opened by a user. When the container is opened, the diminishing gel composition can be activated upon exposure to the open air. It is noted that in some cases, a nominal amount of releasable agent and/or gel-diminishing agent can be found in the headspace of the container. However, the amount of releasable agent and/or gel-diminishing agent found in the headspace of the container is considered to be negligible. Thus, "activation" of the diminishing gel composition or gel-diminishing agent is considered to occur when the gas-tight container is opened and the composition is exposed to open air. Activation of the gel-diminishing agent can cause a gradual decrease in volume and/or mass of the diminishing gel composition. In some examples, the container can be pressurized to minimize the amount of fragrance or gel-diminishing agent that is released into the headspace of the container.

The container can be made of a variety of materials. In some examples, the container can include a material such as polyethylene, polypropylene, polystyrene, ethylene vinyl alcohol, glass, metals such as titanium and aluminum, metal oxides such as alumina, metal alloys such as stainless steel, the like, and combinations thereof.

In some embodiments, the container may have a marking or other indicator that provides a reference point for an original size of a diminishing gel. Accordingly, the container can include an indicator that measures depletion of the releasable agent by comparison of the indicator to the size of the gel composition. The reference point or indicator can be used to reference a decrease in size or volume of the gel composition by visually comparing it to the gel composition. In some embodiments, the indicator or reference point may be the size or other structure of the container itself. In some examples, the measure of depletion can signify that an effective amount of the releasable agent is no longer provided by the gel composition.

The present disclosure additionally encompasses a variety of methods relating to the diminishing gel compositions. In one example, a method of diminishing a volume of a gel composition is provided. In such a method, a gel-diminishing agent can be included as a component of the gel composition. The gel-diminishing agent can gradually diminish the volume or size of the gel composition during use of the gel composition. In one example, the use of the gel composition can commence when a gas-tight container housing or enclosing the gel composition is opened. In one example, the volume of the gel composition can diminish by at least 20%, 25%, or 30% over a period of about 42 days. In one example, the mass of the gel can diminish by at least 20%, 30%, 40%, or 45% over a period of about 7 days and at least some of the lost mass can include a portion of the gel-diminishing agent.

In another embodiment, a method of signaling depletion or exhaustion of an effective amount of the releasable agent in the diminishing gel composition is provided. Such a method can include activating a gel-diminishing agent in the gel composition to reduce a volume or size of the gel composition to a visually detectable or noticeable degree. In one example, the reduction in volume of the gel composition can be correlated to an amount of releasable agent remaining in the gel composition. As previously described, a decrease of at least 30%, 40%, 50%, or 60% of the amount of releasable agent initially included in the diminishing gel composition can indicate that an effective amount of the releasable agent is no longer present in the diminishing gel composition. Thus, the reduction of volume in a visually detectible or noticeable degree can be correlated to indicate that an effective amount of releasable agent is no longer present in the diminishing gel composition (i.e. an expiration or end-of-life volume). In one specific example, the volume reduction of the gel composition that signals depletion of an effective amount of releasable agent (i.e. exhaustion thereof) can be at least 10%, 20%, 25%, or 30% less than the original volume of the gel composition (i.e. 90%, 80%, 75%, or 70% or less of the original volume of the gel composition). The original volume can be the volume of the gel composition present when a user initially opens a gas-tight container housing or enclosing the gel composition.

Another embodiment describes a method of extending release of a releasable agent from a gel composition. In such a method a gel-diminishing agent can be included in the gel composition, wherein the inclusion of the gel-diminishing agent in the gel composition can provide extended release of the releasable agent as compared to a gel composition without the gel-diminishing agent. In some examples, the inclusion of the gel-diminishing agent in the gel composition can extend the release period of the releasable agent by at least 10%, 20%, 25%, or 30%. In some examples, the inclusion of the gel-diminishing agent in the gel composition can extend the release period of the releasable agent by at least 5 days, 10 days, or 15 days. In some examples, the gel-diminishing agent can increase the amount of releasable agent thrown from the diminishing gel composition. In some aspects, the gel-diminishing agent can increase the amount of releasable agent thrown or released from the diminishing gel composition by at least 2 wt %, 3 wt %, 5 wt %, or 10 wt %. The extent to which the diminishing gel composition increases the amount thrown from the composition can depend on the releasable agent used and the gel-diminishing agent used. In some examples, the gel-diminishing agent can cause the gel composition to become more porous. In some examples, the increased porosity of the gel composition can facilitate release of the releasable agent. In some examples, at least a portion of the gel-diminishing agent can evaporate from the gel composition. In yet other examples, evaporation of the gel-diminishing agent can facilitate release of the releasable agent.

Methods of manufacturing a diminishing gel composition are also encompassed by the present disclosure. In one example, such a method can include admixing a gel-diminishing agent with a polymer, such as a gel-forming polymer, and a carrier solvent to form a mixture and allowing the mixture to gelatinize. In some examples, a cross-linking agent can be used to facilitate gelatinization and can be added to the admixture of the gel-diminishing agent and polymer. In some cases, the cross-linking agent can be thermally activated. In some cases, the cross-linking agent does not require addition of heat for activation. In some examples, a releasable agent can be included in the composition, such as a fragrance, a pest repellant, etc. The releasable agent can be added to during the admixing step described above or later in the manufacturing process. In some examples, the diminishing gel composition can be manufactured at room temperature. In some examples, the diminishing gel composition can be manufactured at a sub-ambient temperature, such as 20° C. or below, 15° C. or below, or 10° C. or below. In some cases, mixing at a sub-ambient temperature can help prevent evaporation of the releasable agent. In some examples, the diminishing gel composition can be mixed at a rotational velocity of at least 200 revolutions per minute (rpm), at least 300 rpm, at least 400 rpm, or at least 500 rpm.

In one specific example, a fragrance oil can be added to a liquid polyamide polyamine component and mixed at approximately 300 to 350 rpm. While continuously mixing, a carrier solvent or diluent, such as a C12-C15 alkyl benzoate, can then be added to the mixture. Subsequently, a cyclopentasiloxane can be added to the mixture. Finally, an aliphatic polyisocyanate can be added to the mixture to facilitate curing of the composition. The final composition can then be poured into a container, mold, or other receptacle and allowed to cure for about 3 to 6 hours.

EXAMPLES

Example 1—Gel-Diminishing Agent Facilitates Reduction in Volume of Gel Composition Two fragrance-loaded gel compositions were prepared for comparison. The first composition (Prototype 1A) included 20 wt % polyamide polyamine (CrystaSense®IM700, commercially available from Croda), 70 wt % fragrance, 4 wt % aliphatic polyisocyanate (Desmodur®N3300A, commercially available from Bayer), and 6 wt % C12-C15 alkyl benzoate (Crodamol®AB, commercially available from Croda).

The second composition (Prototype S2A) included equivalent amounts of polyamide polyamine, fragrance, and aliphatic polyisocyanate. The C12-C15 alkyl benzoate was correspondingly reduced to prepare gel compositions at 0.5 wt %, 1 wt %, and 5 wt % cyclopentasiloxane (Xiameter® PMX-245, commercially available from Dow).

Figure 1A:
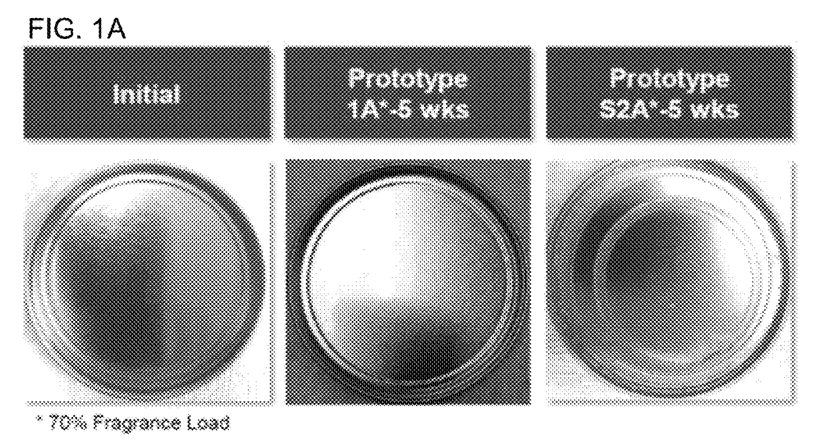
FIG. 1A shows an initial appearance of a gel formulated either with or without a gel-diminishing agent, followed by appearance of the gel without a gel-diminishing agent (1A) and with a gel-diminishing agent (S2A) after 5-6 weeks of exposure to ambient air.

Each gel composition was formed in respective receptacles and allowed to sit, exposed to air, for a period of five to six weeks. FIG. 1A shows the visual appearance of either gel (which were identical) in an initial state, followed by the visual appearance of each gel after the 5-6 week testing period. All S2A prototypes exhibited a visually detectible gradual decrease or reduction in volume or size. As illustrated in FIG. 1A, an example S2A prototype is shown having a visually noticeable or detectible decreased volume or size as compared to the initial volume. Comparatively speaking, the 1A prototype, which does not include a gel-diminishing agent, such as cyclopentasiloxane, did not display a visually noticeable or detectible decrease in volume or size over the five week period.

Figure 1B:
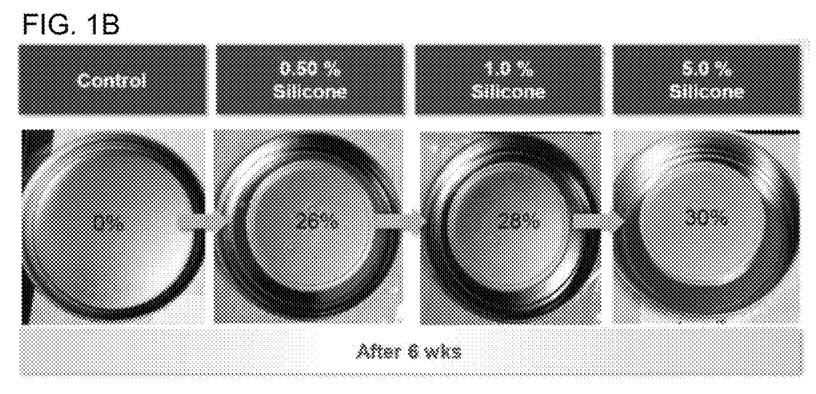
FIG. 1B shows the comparative appearance of a gel with no gel-diminishing agent and three other gels with varying amounts of a gel-diminishing agent after 5-6 weeks of exposure to ambient air.

Additional gels were prepared in accordance with composition (Prototype S2A) above, except that the amount of gel-diminishing agent was varied. FIG. 1B shows the visual appearance of each gel after 6 weeks of exposure to air. As illustrated in FIG. 1B, increasing the amount of gel-diminishing agent, in this case cyclopentasiloxane, can increase the extent to which the gel composition decreases in volume or size over time. More specifically, S2A prototypes having 0.5 wt %, 1 wt %, or 5 wt % exhibited a 26%, 28%, and 30% reduction in volume or size, respectively, over a six-week period of exposure to ambient air and the variations in size reduction are visually noticeable or detectible.

Figure 2:
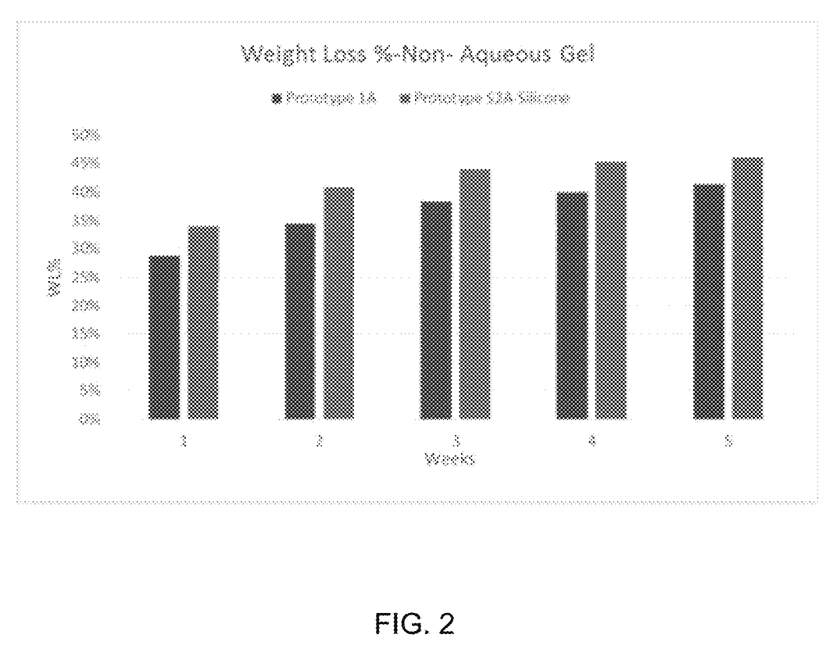
FIG. 2 shows a graphical representation of comparative weight loss over time between a gel with a diminishing agent and a gel without a diminishing agent, but otherwise having substantially identical compositions.

Example 2—Gel-Diminishing Agent Facilitates Reduction in Mass of Gel Composition In connection with Example 1, prototype 1A was compared to prototype S2A, having 5 wt % cyclopentasiloxane, to determine the relative weight loss of each product. Both products were exposed to ambient air for a period of 5 weeks and weighed at one-week intervals during the study. As illustrated in FIG. 2, both products experienced lost mass over time, but prototype S2A experienced greater weight loss than prototype 1A. Both products were designed to release fragrance over time, so it is not surprising that both prototypes showed a decrease in mass over time. However, it is noteworthy that the S2A prototype lost more mass at each testing interval than the 1A prototype.

Example 3—Gel-Diminishing Agent Facilitates Reduction in Volume of Gel Composition In connection with Examples 1 and 2, prototype 1A was compared to prototype S2A, having 5 wt % cyclopentasiloxane, to determine the length of life of each of the prototypes. In this particular study, each prototype was placed in a respective study room for a period of 5 weeks and exposed to ambient air. At one-week intervals, a number of analysts would enter each study room to evaluate the intensity of the fragrance throw at each time point.

Figure 3:
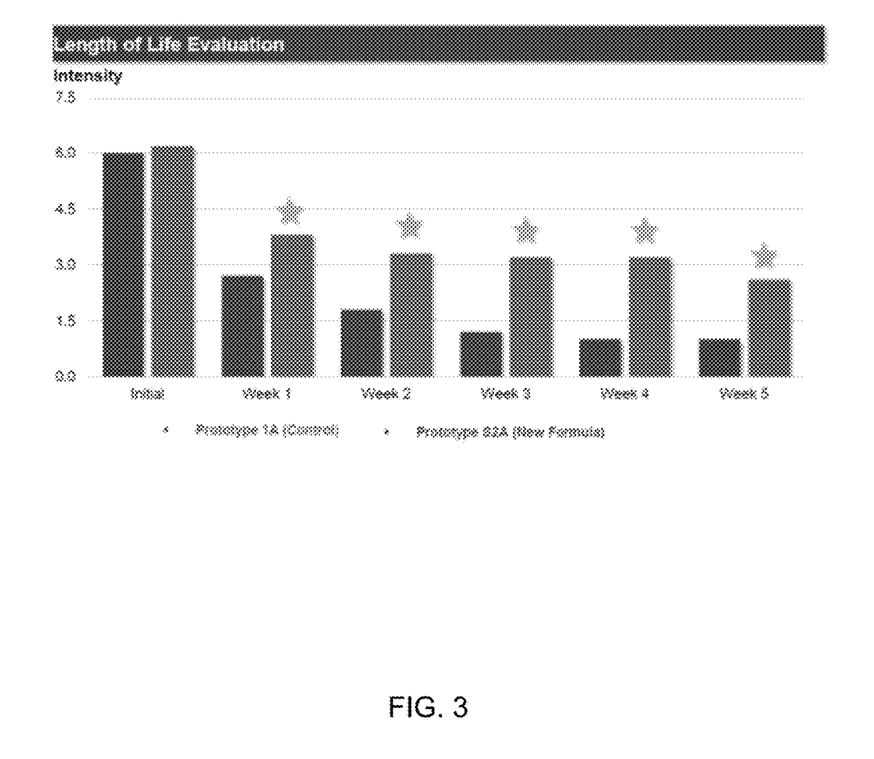
FIG. 3 shows a graphical representation of the comparative change in fragrance intensity over time between a gel with a diminishing agent and a gel without a diminishing agent, but otherwise having substantially identical compositions.

As illustrated in FIG. 3, prototype 1A experienced a much more rapid decrease in fragrance throw over time than prototype S2A. Surprisingly, from weeks 3 to 5, prototype S2A exhibited a fragrance throw intensity that was approximately double that of the 1A prototype. Thus, while the 1A prototype was approaching a reduction in fragrance throw intensity of about 75-85% by week 5, the S2A prototype had only experienced a reduction in fragrance throw intensity of about 50-60%. Accordingly, it is expected that a composition that includes a gel-diminishing agent can extend the release of the fragrance by at least 25%. In some cases, this can equate to extending the release period (i.e. effective useful lifespan) for 10-15 days or more.

It should be understood that the above-described methods are only illustrative of some embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

What is claimed is:

1. A diminishing gel composition, comprising:
    a polymer matrix, said polymer matrix including a polymer having repeating monomer units, wherein the repeating monomer units are terminated by amine groups;
    0.01 wt % to about 10 wt % of, based on the total weight of the composition, a gel-diminishing agent that facilitates a gradual decrease in volume of the gel composition while in use, said gel-diminishing agent being selected from the group consisting of cyclohexasiloxane, cyclopentasiloxane, cyclotetrasiloxane, cyclic polydimethylsiloxane, linear polydimethylsiloxane, hexamethyldisiloxane, and combinations thereof; and
    a releasable active agent which is released in an effective amount from the composition, said releasable active agent being selected from the group consisting of: a fragrance, a pest repellant, a therapeutic agent, a pesticide, and combinations thereof.

2. The composition of claim 1, wherein the polymer matrix includes a polymer and a carrier solvent selected from the group consisting of water, organic solvent, a surfactant, an antioxidant, or a combination thereof.

3. The composition of claim 2, wherein the polymer is present in an amount of from about 1 wt % to about 50 wt %, based on the total weight of the composition.

4. The composition of claim 2, wherein the carrier solvent is present in an amount of from about 0.01 wt % to about 30 wt %, based on the total weight of the composition.

5. The composition of claim 1, wherein the polymer is a polyamine that has an amine number of from about 10 to about 100 milliequivalents (meq).

6. The composition of claim 1, wherein the polymer is a polyamine that has a weight average molecular weight of from about 4,000 Mw to about 30,000 Mw.

7. The composition of claim 1, wherein the polymer is a polyamine that is a blend of at least two different polyamines.

8. The composition of claim 1, wherein the gel-diminishing agent is present in the gel composition in an amount to decrease the volume of the gel composition by at least 20% over a period of about 42 days from activation of the gel-diminishing agent.

9. The composition of claim 1, wherein the gel-diminishing agent is present in the gel composition in an amount to extend effective release of the releasable active agent by at least 5% as compared to a gel composition without the gel-diminishing agent.

10. The composition of claim 1, wherein the releasable active agent is present in an amount of from about 0.01 wt % to about 90 wt %, based on the total weight of the composition.

11. A method of manufacturing a diminishing gel composition, comprising:
    admixing a gel-diminishing agent selected from the group consisting of: cyclohexasiloxane, cyclopentasiloxane, cyclotetrasiloxane, cyclic polydimethylsiloxane, linear polydimethylsiloxane, hexamethyldisiloxane, and combinations thereof, with a gel forming polymer and carrier solvent to form a mixture, said gel-forming polymer having repeating monomer units, wherein the repeating monomer units are terminated by amine groups; and
    allowing the mixture to gelatinize.

12. The method of claim 11, further comprising adding a releasable active agent.

* * * * *